United States Patent [19]

Anderson et al.

[11] 3,943,257

[45] Mar. 9, 1976

[54] 4-ALKYL-4-NAPHTHYL BUTENES

[75] Inventors: Paul L. Anderson, Dover, N.J.; Darryl A. Brittain, New York, N.Y.

[73] Assignee: Sandoz, Inc., E. Hanover, N.J.

[22] Filed: Aug. 20, 1973

[21] Appl. No.: 390,034

[52] U.S. Cl....... 260/483; 260/488 CD; 260/590 D; 260/609 F; 260/613 R; 260/618 D; 260/618 F; 424/317; 424/337; 424/341; 424/343
[51] Int. Cl.$^2$.................. C07C 69/72; C07C 69/02
[58] Field of Search...... 260/488 CD, 613 R, 618 F, 260/618 D, 483, 609 F

[56] References Cited
UNITED STATES PATENTS 2,547,123  4/1951  Horeau et al................... 260/473 F
3,562,336  2/1971  Nelson............................... 260/613

OTHER PUBLICATIONS

Burton, Chem. Abstracts, Vol. 25, (1931), p. 3329.

Primary Examiner—James A. Patten
Attorney, Agent, or Firm—Gerald D. Sharkin; Richard E. Vila; Frederick H. Weinfeldt

[57] ABSTRACT

The compounds are 4-naphthyl-4-lower alkyl substituted-2-oxygenated-2-butenes, or butanes; the naphthyl position may be unsubstituted or 6-substituted, e.g., 2-(6-methoxynaphthyl)-2-penten-4-ol, and are useful as pharmaceuticals.

9 Claims, No Drawings

4-ALKYL-4-NAPHTHYL BUTENES

This invention relates to chemical compounds, and more particularly, to 4-alkyl-4-naphthyl substituted-butanes and compounds related thereto, and to the preparation of such compounds and intermediates in said preparation, as well as to pharmaceutical compositions containing such compounds and the use of such compounds.

The compounds of this invention may be conveniently represented by the formula I:

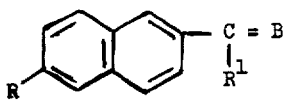

wherein
R is a hydrogen atom or halo having an atomic weight of from about 19 to 80, i.e., fluoro, chloro or bromo, lower alkyl, lower alkoxy, lower alkylthio, or difluoromethoxy;
$R^1$ is lower alkyl, e.g., having from 1 to 3 carbon atoms, such as methyl, ethyl, n-propyl and isopropyl; and
B is either of the structures:

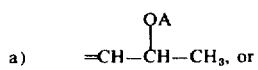

a)

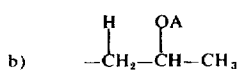

b)

wherein
A is a hydrogen atom, or lower acyl, e.g. having from 2 to 4 carbon atoms such as acetyl, propionyl or butyryl, including isomeric forms, but is preferably unbranched, or acetoacetyl.

In the definitions of R, above, the terms lower alkyl, lower alkoxy and lower alkylthio, the alkyl portion has, e.g., from 1 to 4 carbon atoms, such as methyl, ethyl, propyl or butyl, including isomeric forms where such exist, but are preferably unbranched. The term R, therefore, may alternatively be defined as being a hydrogen atom, halo having an atomic weight of from about 19 to 80, difluoromethoxy or the structure

wherein X is either a single bond, or an oxygen or sulfur atom, and R' is lower alkyl, as defined above.

The class of Compounds I, thus includes 4 subclasses depending upon the nature of B; $R^1$ and R being as defined above, and A' being A when it is not a hydrogen atom, i.e. when it is lower acyl:

Ia1

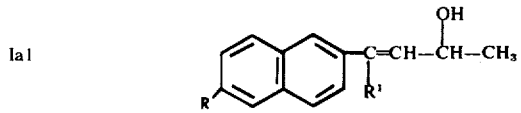

Ia2

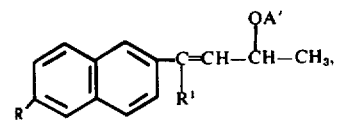

Ib1

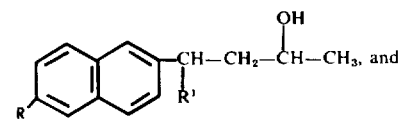

Ib2

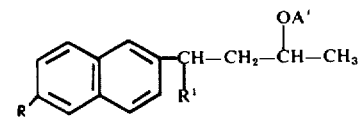

Compounds Ia2 and Ib2, are acylated derivatives of compounds Ia1 and Ib1, respectively, obtainable by acylating Compounds Ia1 or Ib1 (process 1). Conversely, Compounds Ia1 and Ib1 may be obtained by saponification of the corresponding Compounds Ia2 and Ib2, respectively (process 2). Compounds I are thus interconvertible.

Compounds Ib1 are obtainable by reducing the unsaturation of a corresponding Compound Ia1 (process a).

Compounds Ia1 are obtainable by reducing the carbonyl function of Compounds II (process b), i.e., 4-substituted-phenyl-4-alkyl-3-buten2-ones of the formula:

II

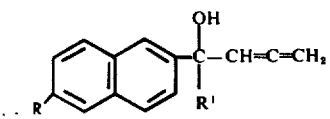

wherein R and $R^1$ are as defined above.

Compounds II are obtainable by acidic treatment (process c) of compounds III, i.e. 1-substituted-phenyl-1-alkyl-2,3-butadien-1-ols:

III

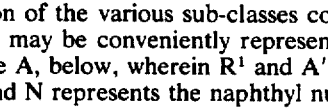

wherein R and $R^1$ are as defined above.

The preparation of the various sub-classes comprising compounds I may be conveniently represented by Reaction Scheme A, below, wherein $R^1$ and A' are as defined above and N represents the naphthyl nucleus

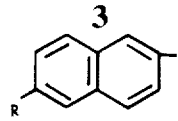

; wherein R is as defined above;

for such a reaction. The process is suitably effected in an inert organic solvent, such as benzene, toluene or a mixture thereof, and in the presence of a small amount of an organic tertiary amine. e.g., pyridine. The process is conveniently carried out at a relatively low temperature, e.g., from −5° to +35° C.

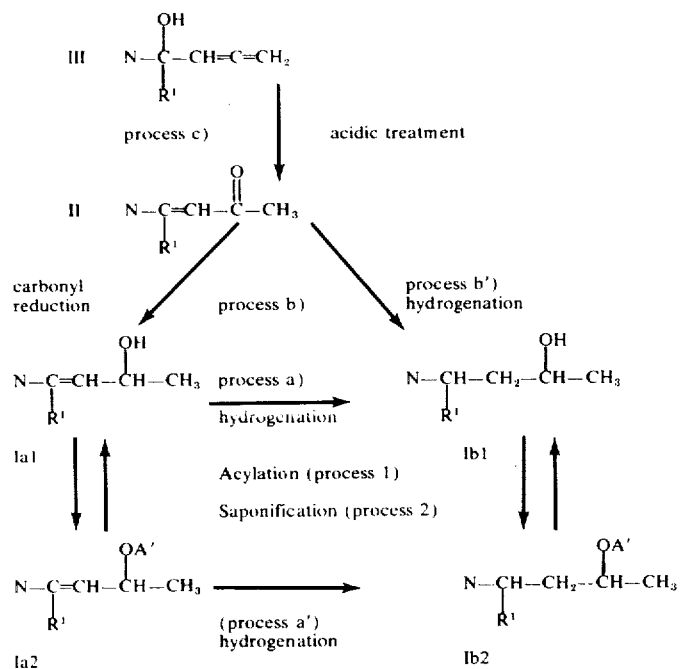

The acylation of compounds Ia1 or Ib1 (process 1); may be carried out by conventional techniques. The acylation, thus, may be effected by processes known per se for the acylation of secondary aliphatic alcohols. Suitable alkanoylating agents include organic acids, acyl halides and acid anhydrides of formulae Ac-OH, Ac-Hal and (Ac)$_2$O, respectively, wherein Ac is a lower alkanoyl group suitable as A when it is a lower alkanoyl group as defined above, and Hal signifies bromine or chlorine, and mixtures thereof. Where the desired alkanoyl moiety is acetyl, a preferred acylating agent is acetic anhydride. In carrying out the alkanoylation inert solvent may be employed or excess alkanoylating agent may serve as solvent. An acid binding agent, e.g., pyridine, is preferably used. Preferred temperatures vary between −10 and 50° C. If desired, more stringent conditions may be used, characterized by the presence of a strongly acidic catalyst, e.g., p-toluene-sulphonic acid. If such catalysts are used, in addition to the above-listed alkanoylating agents, enol acylates, preferably esters of "isopropenyl alcohol", e.g. isopropenyl acetate, may also be employed. The considerations involved are well within the scope of one skilled in the art. The formation of a acetoacetyloxy function may be carried out by reacting a compound Ia1 or Ib1 with diketene under conventional conditions The acylated forms of Compounds I, i.e., Compounds Ia2 and Ib2, may be saponified (process 2) employing conventional means, e.g., by treatment with dilute sodium hydroxide or methanolic potassium bicarbonate, to obtain a corresponding hydroxy-bearing Compound I, i.e., Compounds Ia1 and Ib1.

Process (a) involves the reduction of the unsaturated position of a Compound Ia1 to obtain the corresponding Compound Ib1. The process may be carried out by treating a Compound Ia1 with hydrogen at moderate pressures, e.g., at about 1 atmosphere. The process may be carried out in an inert solvent, e.g., a lower alkanol, such as methanol, ethyl acetate, benzene, glyme, or dioxane, at moderate temperatures, e.g., from about −20° to +30° C., preferably at room temperature (20° to 30° C.), employing a conventional hydrogenation catalyst, e.g., 10% palladium on charcoal. Other catalysts such as palladium on an inert carrier such as barium carbonate, may similarly be used.

Process (b) involves reducing the carbonyl function of a Compound II to obtain the corresponding Compound Ia1. The reduction may be carried out using conventional techniques for the reduction of an aliphatic ketone to its corresponding alcohol. For example, a complex metal hydride, such as sodium aluminum diethyl dihydride or lithium aluminum tri-t-butoxy hydride may be employed in a suitable medium, e.g., an ether, such as diethyl ether, tetrahydrofuran, or dioxane, or an aromatic medium, such as benzene, toluene or pyridine, the medium may be a single material or a mixture. The reaction may be conveniently carried out at temperatures of from about −10° to 40° C., preferably at about −5° to +15°C.

Alternatively, subjecting a Compound II to the reducing conditions of process (a) yields the corresponding Compound Ib1 (process b'), thus by-passing process (b). Furthermore, if desired, a Compound Ia2 may be subject to the reducing conditions of process (a) to obtain the corresponding Compound Ib2, (process a').

Process (c) involves acidic treatment of a Compound III to obtain the corresponding Compound II, and may be carried out employing as the "acidic" source a strong protonating agent in the presence of hydroxy, (lower) acyloxy or (lower) alkoxy anion, in a suitable medium, at moderate temperatures, e.g., 10° to 100° C., preferably at 15° to 35° C. Where the hydroxy, (lower) acyloxy or (lower) alkoxy contributing agent is a liquid under the process conditions, it may be used in excess to serve as the medium.

Strong protonating agents include mineral acids, such as hydrochloric or hydrobromic, or sulfuric acid, and aromatic- or (lower) aliphatic sulfonic acids, such as p-toluenesulfonic acid. Suitable hydroxy, (lower) acyloxy, e.g., having 2 to 4 carbon atoms, and (lower) alkoxy anion, e.g., having from 1 to 4 carbon atoms, contributing agents include lower alkanols, such as methanol, esters such as ethyl orthoformate, or organic acids or anhydrides, such as acetic acid or acetic anhydride, singly or in mixtures.

If hydrochloric (or hydrobromic) acid is employed as the acidic source in process c), then in addition to the corresponding Compound II product, a corresponding 4-substituted-phenyl-4-alkyl-2-chloro-(or bromo)-1,3-butadiene co-product will also be formed. The products can be separated so as to recover the Compound II product, by conventional recovery procedures, such as fractional crystallization and chromatographic techniques.

Compounds III, the starting materials of Process (a) are either known compounds or analogs of known compounds and are obtainable by adaption of the methods described in the literature for the preparation of such compounds, e.g. the Belgian patent issuing on Belgian Application 124,754 (filed Nov. 29, 1972 and claiming priority of U.S. application No. 203,825, filed Dec. 1, 1971).

The compounds of formula I are useful because they possess pharmacological activity in animals. In particular, the compounds I are useful as anti-inflammatory agents as indicated by the Carrageenan induced edema test on rats (oral administration at 5 to 200 mg/kg). For such use, the compounds may be combined with a pharmaceutically acceptable carrier, and such other conventional adjuvants as may be necessary, and administration orally in such forms as tablets, capsules, elixirs, suspensions and the like or parenterally in the form of an injectable solution or suspension. The dosage administered will, of course, vary depending upon the compounds used and the mode of administration. However, in general, satisfactory results are obtained when administered at a daily dosage of from about 0.5 milligram to about 175 milligrams per kilogram of body weight, preferably given in divided doses 2 to 4 times a day, or in sustained release form. For most mammals the administration of from about 30 milligrams to about 2000 milligrams of the compound per day provides satisfactory results and dosage forms suitable for internal administration comprise from about 8 milligrams to about 1000 milligrams of the compound in admixture with a solid or liquid pharmaceutical carrier or diluent.

As noted above, oral administration with carriers may take place in such conventional forms as tablets, dispersible powders, granules, capsules, syrups and elixirs. Such compositions may be prepared according to any method known in the art for manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g. suspending agents (methyl-cellulose, tragacanth and sodium alginate), wetting agents (lecithin, polyoxyethylene stearate and polyoxyethylene sorbitan monooleate) and preservatives (ethyl-p-hydroxybenzoate). Capsules preferably contain the active ingredient admixed with an inert diluent, e.g. a solid diluent such as calcium carbonate, calcium phosphate and kaolin or a liquid diluent such as a polyethylene glycol. The preferred pharmaceutical compositions from the standpoint of preparation and ease of preparation and ease of administration are orally administrable compositions, particularly tablets and liquid or solid diluent-filled capsules.

Representative formulations of a tablet and a capsule prepared by conventional techniques are as follows:

| Ingredient | Weight Tablet | Capsule |
|---|---|---|
| 2-[2-(6-methoxynaphthyl)]-2-penten-4-ol | 50 | 50 |
| Tragacanth | 10 | — |
| Lactose | 197.5 | 250 |
| Corn Starch | 25 | — |
| Talcum | 15 | — |
| Magnesium Stearate | 2.5 | — |

In the following examples, which illustrate the invention, temperatures are in degrees centigrade, and room temperature is 20° to 30°C., unless indicated otherwise.

EXAMPLE 1.

2-[2-(6-methoxynaphthyl)]-2-penten-4-ol.

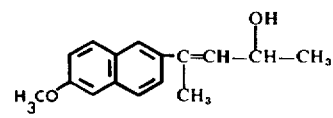

Step (A) 2-[2-(6-methoxynaphthyl)]-2-penten-4-one.

To a solution of 10 g. of 2-[2-(6-methoxynaphthyl)]-3,4-pentadien-2-ol in 200 ml. of anhydrous methanol is added 3 ml. of concentrated hydrochloric acid (12N). The mixture is stirred at room temperature for 3 hours and then at ice bath temperature for 2 hours.

Repeating the procedures of Example 1 and of this example, but using in place of the 2-[2-(6-methoxynaphthyl)]-3,4-pentadien-2-ol (of Example 1), an equivalent amount of the compound of column (A) there is similarly obtained the compounds of columns (B) and (C):

|   | A | B | C |
|---|---|---|---|
| a) | 2-[2-(6-chloro naphthyl)]-3,4-pentadien-2-ol | 2-[2-(6-chloro-naphthyl)]-2-penten-4-ol | 2-[2-(6-chloro-naphthyl)]-pentan-4-ol |
| b) | 2-(2-naphthyl)-3,4-pentadien-2-ol | 2-(2-naphthyl)-2-penten-4-ol | 2-(2-naphthyl)-pentan-4-ol |
| c) | 3-[2-(6-methoxy-naphthyl)]-2-methyl-4,5-hexadien-3-ol | 3-[2-(6-methoxy-naphthyl)]-2-methyl-3-hexen-5-ol | 2-[2-(6-methoxy-naphthyl)]-2-methyl-hexan-5-ol |
| d) | 3-[2-(6-methoxy-naphthyl)]-4,5-hexadien-3-ol | 3-[2-(6-methoxy-naphthyl)]-3-hexen-5-ol | 2-[2-(6-methoxy-naphthyl)]-hexan-5-ol |
| e) | 2-[2-(6-difluoro-methoxynaphthyl)]-3,4-pentadien-2-ol | 2-[2-(6-difluoro-methoxynaphthyl)]-2-penten-4-ol | 2-[2-(6-difluoro-methoxynaphthyl)]-pentan-4-ol |
| f) | 2-[2-(6-n-butyl-naphthyl)]-3,4-pentadien-2-ol | 2-[2-(6-n-butyl-naphthyl)]-2-penten-4-ol | 2-[2-(6-n-butyl-naphthyl)]-pentan-4-ol |
| g) | 2-[2-(6-methyl-thionaphthyl)]-3,4-pentadien-2-ol | 2-[2-(6-methylthio-naphthyl)]-2-penten-4-ol | 2-[2-(6-methylthio-naphthyl)]-pentan-4-ol |
| h) | 2-[2-(6-ethoxy-naphthyl)]-3,4-pentadien-2-ol | 2-[2-(6-ethoxy-naphthyl)]-2-penten-4-ol | 2-[2-(6-ethoxynaphthyl)] pentan-4-ol |

The solid which forms is filtered off and recrystallized from pentane to give 2-[2-(6-methoxynaphthyl)]-2-penten-4-one, m.p. 108°–109°C.

Step (B) 2-[2-(6-methoxynaphthyl)]-2-penten-4-ol.

To a solution of 3.g. of 2-[2-(6-methoxynaphthyl)]-2-penten-4-one in 50 ml. of ethyl ether, at 0°C., 20 ml. of sodium aluminum diethyl dihydride in toluene is dropwise added. After 2 hours at 0°C., the mixture is poured onto ice and extracted with ether to give a light yellow solid. Crystallization from methylene chloride yields 2-[2-(6-methoxynaphthyl)]-2-penten-4-ol, m.p. 139°–140°C., which may also be designated 2-[2'-(6'-methoxynaphthyl)]-pent-2-en-4-ol, or 2-[2-(6-methoxynaphthyl)]-3-penten-2-ol.

EXAMPLE 2.

2-[2-(6-methoxynaphthyl)]-pentan-4-ol.

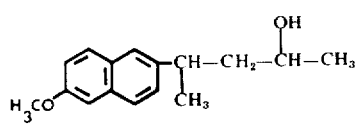

To a pressure vessel, mixture of 0.7 g. of 2-[2-(6-methoxynaphthyl)]-2-penten-4-ol (obtainable by Example 1) and 0.5 g. of 10% palladium on carbon in 175 ml. of ethanol, is added hydrogen at about 1 at. pressure via low pressure hydrogenation. The catalyst is then removed, and the solution is evaporated to give a colorless oil which solidifies on standing to give solid 2-[2-(6-methoxynaphthyl)]-pentan-4-ol, which may also be designated 4-[2-(6-methoxynaphthyl)]-pentan-2ol.

EXAMPLE 3.

4-acetoxy-2-[2'-(6'-methoxy-naphthyl)]-pent-2-ene.

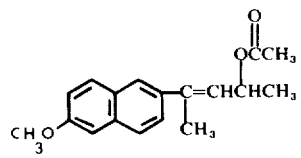

To a solution of 0.550 gram of 2-[2-(6-methoxynaphthyl)]-2-penten-4-ol (obtainable by Example 1) in 150 ml. dry pyridine, 10 ml. of acetic anhydride is added. After standing 18 hours at room temperature, the solution is poured onto ice. The precipitated solid is filtered from the mixture, then dissolved in diethyl ether. The resulting solution is washed successively with water, 10% aq. sodium bicarbonate solution, and then brine. The solution is dried over anhydrous potassium carbonate. The drying agent is removed by filtration, and the filtrate is evaporated under reduced pressure to yield 4-acetoxy-2-[2'-(6'-methoxynaphthyl)]-pent-2-ene as a white electrostatic solid of melting point, 80°C., which may also be designated 2-[2-(6-methoxynaphthyl)]-2-penten-4-ol acetate.

Repeating the procedure of this example but using in place of the 2-[2-(6-methoxynaphthyl)]-2-penten-4-ol, an equivalent amount of the compounds listed below, there is similarly obtained the acetates of:

a. 2-[2-(6-methoxynaphthyl)]-pentan-4ol;
b. 2-(2-naphthyl)-2-penten-4ol; and
c. 3-[2-(6-methoxynaphthyl)]-3-hexen-5-ol.

What is claimed is:

1. A compound of the formula

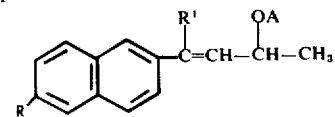

wherein

R is a hydrogen atom, halo having an atomic weight of from about 19 to 80, difluoromethoxy, alkyl having from 1 to 4 carbon atoms, alkoxy having from 1 to 4 carbon atoms, or alkylthio having from 1 to 4 carbon atoms;

$R^1$ is alkyl having from 1 to 3 carbon atoms; and

A is a hydrogen atom, alkanoyl having from 2 to 4 carbon atoms, or acetoacetyl.

2. A compound of claim 1 in which A is either acetoacetyl or alkanoyl.

3. A compound of claim 1 in which A is acetoacetyl.

4. A compound of claim 1 wherein $R^1$ is methyl.

5. A compound of claim 1 wherein R is alkoxy.

6. A compound of claim 1 wherein A is a hydrogen atom.

7. The compound of claim 5 which is 2-[2-(6-methoxynaphthyl)]-2-penten-4ol.

8. A compound of claim 1 wherein A is alkanoyl.

9. The compound of claim 8 which is 4-acetoxy-2-[2'-(6'-methoxynaphthyl)]-pent-2-ene.

* * * * *